United States Patent
Walton, III

(10) Patent No.: US 8,960,555 B1
(45) Date of Patent: *Feb. 24, 2015

(54) MEDICAL INFORMATION DEVICE AND SYSTEM AND METHOD OF USE

(71) Applicant: James F. Walton, III, Tallahassee, FL (US)

(72) Inventor: James F. Walton, III, Tallahassee, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/258,094

(22) Filed: Apr. 22, 2014

Related U.S. Application Data

(63) Continuation-in-part of application No. 14/048,645, filed on Oct. 8, 2013, now Pat. No. 8,740,089.

(51) Int. Cl.
*G06F 19/00* (2011.01)
*G06K 19/06* (2006.01)

(52) U.S. Cl.
CPC ........ *G06F 19/322* (2013.01); *G06K 19/06037* (2013.01)
USPC .......................................................... 235/487

(58) Field of Classification Search
USPC .......................................................... 235/487
See application file for complete search history.

(56) References Cited

U.S. PATENT DOCUMENTS

| | | | |
|---|---|---|---|
| 5,658,016 A | 8/1997 | Goeken | |
| D426,833 S | 6/2000 | Vanelli | |
| 6,513,720 B1 | 2/2003 | Armstrong | |
| 6,747,561 B1 | 6/2004 | Reeves | |
| 6,751,805 B1 | 6/2004 | Austion | |
| 6,845,063 B2 | 1/2005 | Mitchell | |
| 7,827,043 B2 | 11/2010 | Tahan | |
| 8,740,089 B2 * | 6/2014 | Walton, III | ..................... 235/487 |
| 2002/0120470 A1 | 8/2002 | Trice, Sr. | |
| 2003/0058110 A1 | 3/2003 | Rich | |
| 2003/0101077 A1 | 5/2003 | Whol | |
| 2003/0150143 A1 | 8/2003 | Hazard | |
| 2005/0194270 A1 | 9/2005 | Gombar | |
| 2006/0010012 A1 | 1/2006 | Franzblau et al. | |
| 2006/0015368 A1 | 1/2006 | Hockey | |
| 2006/0085226 A1 | 4/2006 | Kamber | |
| 2006/0142057 A1 | 6/2006 | Schuler et al. | |
| 2007/0158411 A1 | 7/2007 | Krieg, Jr. | |
| 2007/0265884 A1 | 11/2007 | Lubell et al. | |
| 2008/0126729 A1 | 5/2008 | Cai et al. | |
| 2008/0288540 A1 * | 11/2008 | Jarvis et al. | ................ 707/104.1 |
| 2008/0319798 A1 | 12/2008 | Kelley | |
| 2009/0076849 A1 | 3/2009 | Diller | |
| 2009/0101721 A1 | 4/2009 | Hawthorne et al. | |
| 2009/0295569 A1 | 12/2009 | Corwin et al. | |
| 2010/0115609 A1 | 5/2010 | Spence | |

* cited by examiner

*Primary Examiner* — Christle I Marshall
(74) *Attorney, Agent, or Firm* — Livingston Loeffler, P.A.; Edward M. Livingston, Esq.; Bryan L. Loeffler, Esq.

(57) ABSTRACT

A medical information device (1) and two dimensional bar code (2) for storing an individual's emergency medical information on and/or providing remote access to the medical information. The medical information device may be updated by an individual over the Internet by sending updated information to a central location that updates the information in a central database. The medical information device is capable of storing medical information directly therein and/or of providing remote access to medical information stored in a central database. This is accomplished by using a two-dimensional barcode 2, such as a Quick Response Code ("QR code") (3) or other matrix barcode, that is capable of storing text and/or URL information that may be opened by an electronic device or other imaging device, such as a smart phone.

10 Claims, 4 Drawing Sheets

US 8,960,555 B1

MEDICAL INFORMATION DEVICE AND SYSTEM AND METHOD OF USE

CROSS-REFERENCE TO RELATED APPLICATIONS

This application is a continuation-in-part of application Ser. No. 14/048,645 filed on Oct. 8, 2013 which is currently pending. The patent application identified above is incorporated herein by reference in its entirety to provide continuity of disclosure.

FIELD OF THE INVENTION

This invention relates to providing personal medical information to first responders during an emergency and other medical personnel through the use of electronic devices and the internet.

BACKGROUND OF THE INVENTION

During a medical emergency, time is of the essence for a patient to receive the proper care from first responders. In such instances it is important that first responders are aware of a patient's medical history including allergies to drugs, current medications and medical conditions. It also becomes necessary to have the patient's emergency contact information and physician contact information. In many instances patients are unconscious and unable to provide any information to first responders. Conventional methods of providing such information include medical identification bracelets which may list an individual's allergies or medical conditions. However, only a limited amount of information can be included on such bracelets. There have also been attempts to store an individual's medical information on electronic storage devices such as flash drives or radio frequency identification cards ("RFID") in the past. However, many of these devices are complicated to use and to store information on. In addition, many of these devices are carried in wallets or on key chains and can easily be missed by a first responder. In addition, such devices may be damaged in certain situations, such as if the devices become wet during a medical emergency involving water or if the devices are near flames. A further problem with conventional devices occurs if an individual is injured in a foreign country, thereby rendering the electronic storage device useless because the information stored on the device is not written in the first responder's native language.

Therefore, the need exists for a personal medical information device and system and method of use that allows a first responder or other medical personnel to access an individual's medical information.

SUMMARY OF THE INVENTION

The primary object of the present invention is to provide a medical information device and system and method of use that allows a user to easily store personal and medical information in a central database.

Another object of the present invention is to provide a medical information device that is easily identifiable by a first responder as being a medical information device.

An additional object of the present invention is to provide a medical information device and system and method of use that provides a medical worker remote access to an individual's medical information.

The present invention fulfills the above and other objects by providing a medical information device for storing emergency medical information, such as blood type, allergies, medical conditions, present medications, age, doctor information and emergency contact information. The card is capable of storing medical information and/or access information so medical information may be accessed remotely. This is accomplished by using a two-dimensional barcode, such as a Quick Response Code ("QR code") or other matrix barcode, that is capable of storing text and/or URL information that may be opened by an electronic device or other imaging device, such as a smart phone. The two-dimensional barcode may be printed directly on a medical information device. Alternatively, the two-dimensional barcode may be printed on a bracelet, key chain and/or on an adhesive-backed material and then adhered to an existing card, such as a driver's license or other identification card, thereby making the existing card a medical information device. Alternatively, the two-dimensional barcode or other readable storage medium may be printed on a sleeve into which an identification card, such as a driver's license is placed.

An additional advantage of the method and system of the present invention is an added layer of security for allowing access to be able to read the storage medium on the medical information device or using the medical information device to access medical information stored remotely.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
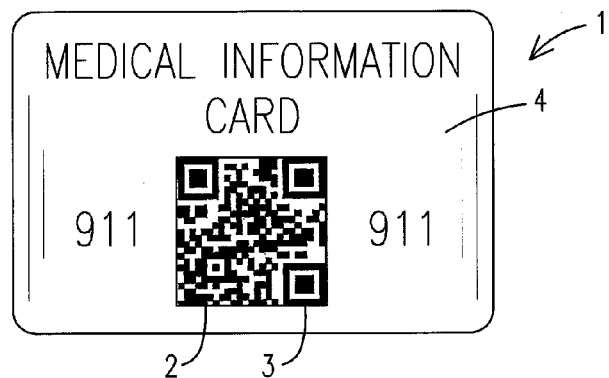
FIG. 1 is a front view of an identification card being used as a medical information device of the present invention.

With reference to FIG. 1, a front view of an identification card 4 being used as a medical information device 1 of the present invention is illustrated. The medical information device 1 allows an individual to store emergency medical information, such as blood type, allergies, medical conditions, present medications, age, doctor information and emergency contact information and to provide a means for retrieving that information to a first responder or other medical personnel. First responders may include certified EMTs, doctors, nurses, dentists, fire fighters, law enforcement, hospital staff, emergency room staff, ambulance staff, home health care providers, family members, next of kin, friends, coaches and so forth. The medical information device 1 is capable of storing medical information directly therein and/or of providing remote access to medical information stored in a central database. This is accomplished by using a two-dimensional barcode 2, such as a Quick Response Code ("QR code") 3 or other matrix barcode, that is capable of storing text and/or URL information that may be opened by an electronic device or other imaging device, such as a smart phone. The two-dimensional barcode 2 may be printed directly on a medical information device 1, such as an identification card 4 (as illustrated here), a bracelet, a keychain, sleeve for an identification card and so forth.

Figure 2:
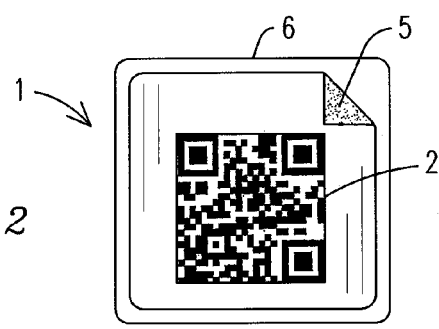
FIG. 2 is a front view of a two-dimensional barcode of the present invention printed on an adhesive-backed material.

With reference to FIG. 2, a front view of a two-dimensional barcode 2 of the present invention printed on an adhesive-backed material 5 is illustrated. The two-dimensional barcode 2 may have medical information directly stored therein and/or provide a URL for remote access of medical information stored in a central database. The two-dimensional barcode 2 illustrated here may be used by peeling off a backing 6 and adhering the adhesive backed material 5, such as paper, plastic, foil and so forth, to any object, such as an identification card, bracelet, keychain and so forth, sleeve for an identification card thereby making the object a medical information device 1.

Figure 3A:
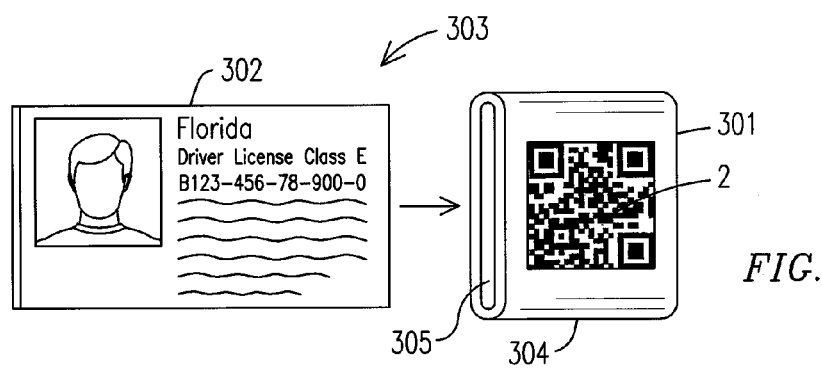
FIG. 3A is an exploded front perspective view of a sleeve for an identification card being used as a medical information device of the present invention.
Figure 3B:
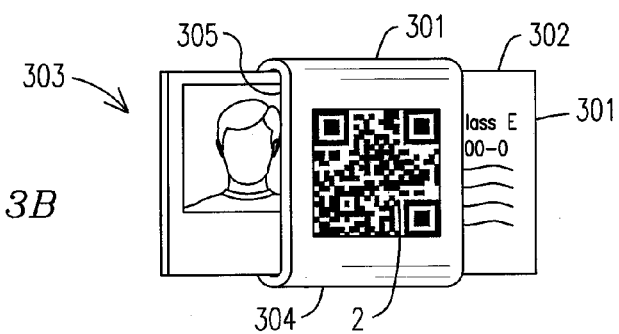
FIG. 3B is a front perspective view of a sleeve for an identification card being used as a medical information device of the present invention.

With reference to FIGS. 3A and 3B, an exploded front perspective view and a front perspective view, respectively, of a sleeve 301 for an identification card 302 being used as a medical information device 303 of the present invention are illustrated. The sleeve 301 comprises a perimeter wall 304 having at least one opening 305 to allow the identification card 302 to be inserted into the sleeve 301. A two-dimensional barcode 2 or other readable electronic medium may be printed directly on the sleeve 301 or adhered to the sleeve 301 like a sticker.

Figure 4:
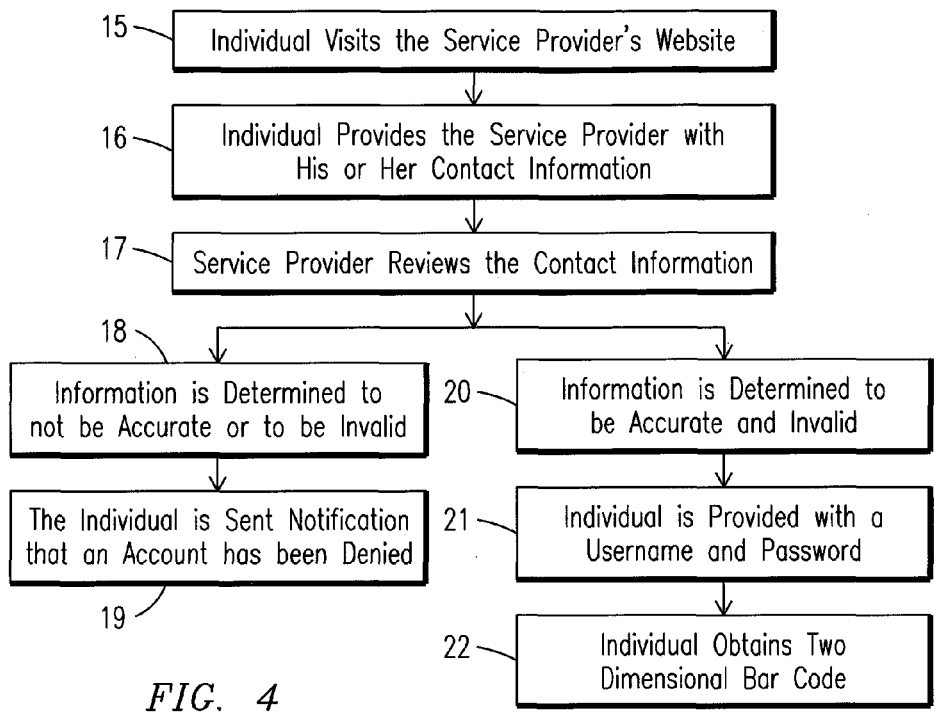
FIG. 4 is a flow chart showing an individual signing up for an account with a service provider that provides a medical information device to the individual.

With reference to FIG. 4, a flow chart showing an individual signing up for an account with a service provider that provides a medical information device to the individual is illustrated. First, the individual visits the service provider's website 15. Then, the individual provides the service provider with his or her contact information, which includes the individual's name, address, phone number, email address and so forth 16. The service provider then reviews the contact information to determine the accuracy of the information and the validity of the information 17. If the information is determined to not be accurate or to be invalid 18, then the individual is sent notification, preferably via email, that an account has been denied 19. If the information is determined to be accurate and valid 20, then the individual is sent an approval, preferably via email, that an account has been created and the individual is provided with a username and password 21. Next, the individual is provided with a medical information device having a two dimensional barcode printed thereon and/or with a adhesive backed two dimensional barcode 22.

Figure 5:
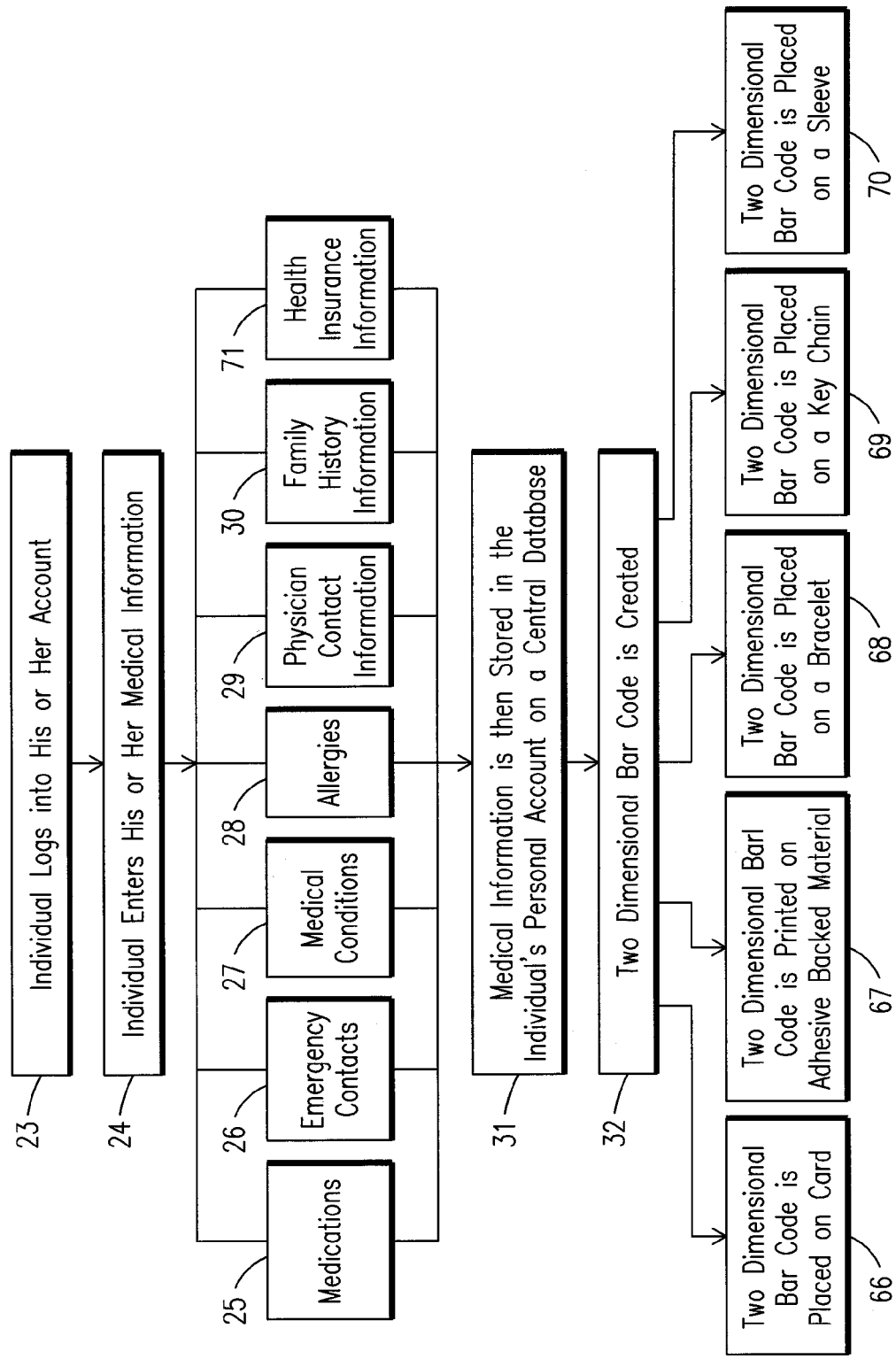
FIG. 5 is a flow chart showing the system and method of the present invention in which an individual enters medical information into an online account.

With reference to FIG. 5, a flow chart showing the system and method of the present invention in which an individual enters medical information into an online account is illustrated. First, the individual logs into his or her account using the username and password provided by the service provider 23. Then, the individual enters his or her medical information 24, which includes medications 25, emergency contacts 26, medical conditions 27, allergies 28, physician contact information 29, family history information 30, health insurance information 71 and so forth. The medical information is then stored in the individual's personal account on a central database 31. A two dimensional bar code is then created that is personalized to the individual's account and has text medical information and/or a URL that directs a user to the individual's medical information remotely after the two dimensional bar code is scanned 32. The two dimensional bar code may be printed on an identification card 66, an adhesive backed material 67, a bracelet 68, a keychain 69, and/or a sleeve 70.

Figure 6:
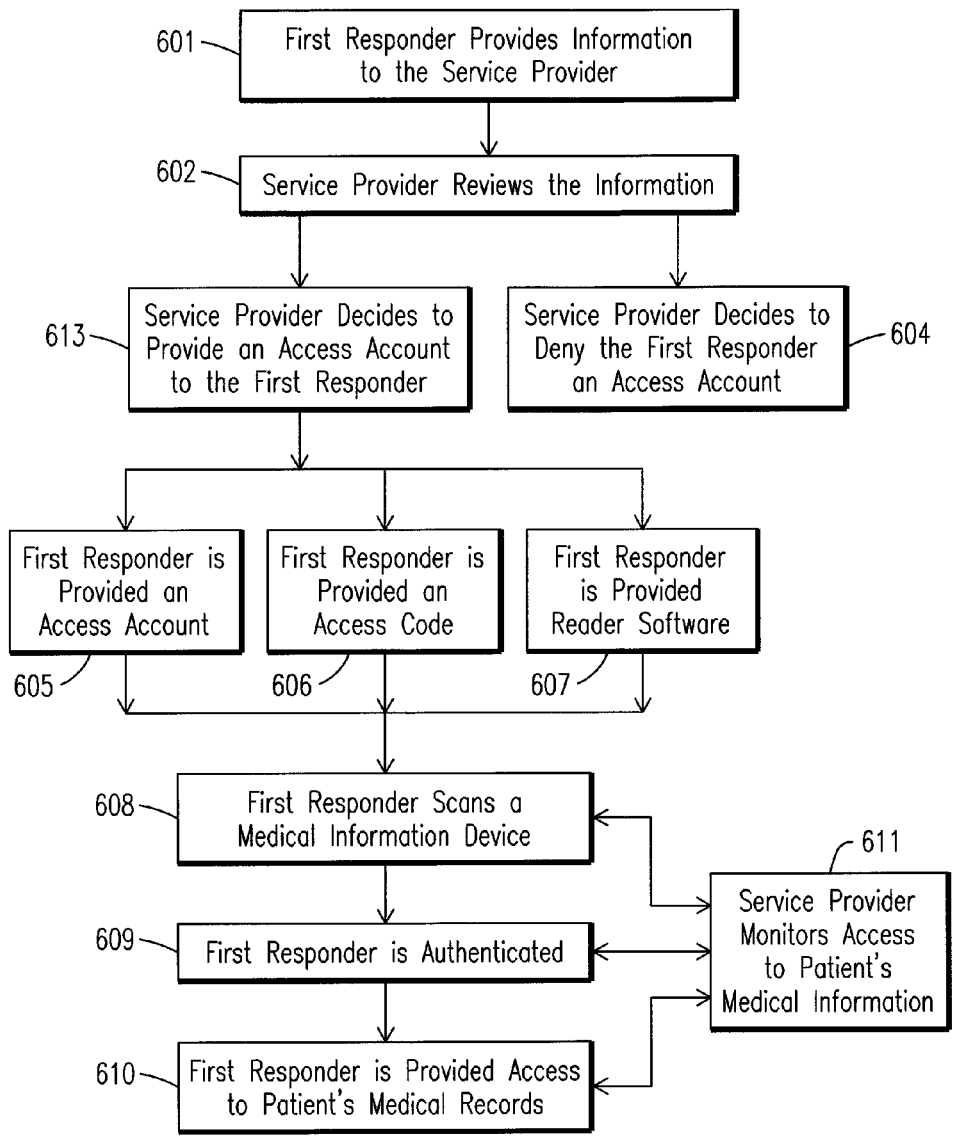
FIG. 6 is a flowchart showing the system and method of the present invention in which a first responder (or other medical personnel) is provided an account with the service provider to allow the first responder to read medical information stored on a patient's medical information device and/or to access information remotely from the central database.

With reference to FIG. 6, a flowchart showing the system and method of the present invention in which a first responder (or other medical personnel) is provided an account with the service provider to allow the first responder to read medical information stored on a patient's medical information device and/or to access information remotely from the central database is illustrated. First, the first responder provides information, such as name, address, employer, position and so forth, to the service provider 601. Then, the service provider reviews the information and determines if the information is correct and accurate 602. Next, the service provider decides to provide an access account to the first responder 603 or denies the first responder an access account 604. If the service provider decides to provide an access account to the first responder 603, then the first responder is provided an access account 605, provided an access code 606 and/or provided reader software 607 (such as electronic scanning and reading software for bar codes, QR codes and so forth) to allow the first responder to read medical information stored on a patient's medical information device and/or to access information remotely from the central database. When the first responder scans an electronic storage means on a medical information device with an electronic device (such as a smart phone) using the reader software 608, the first responder is required to enter the access code or to be authenticated 609 prior access any medical information stored directly on the medical information device and/or accessing information remotely from the central database 610. The service provider is then able to ensure that medical information is kept private. In addition, the service provider is able to monitor who is accessing a patient's medical information and when and where the medical information is being accessed 611.

Figure 7:
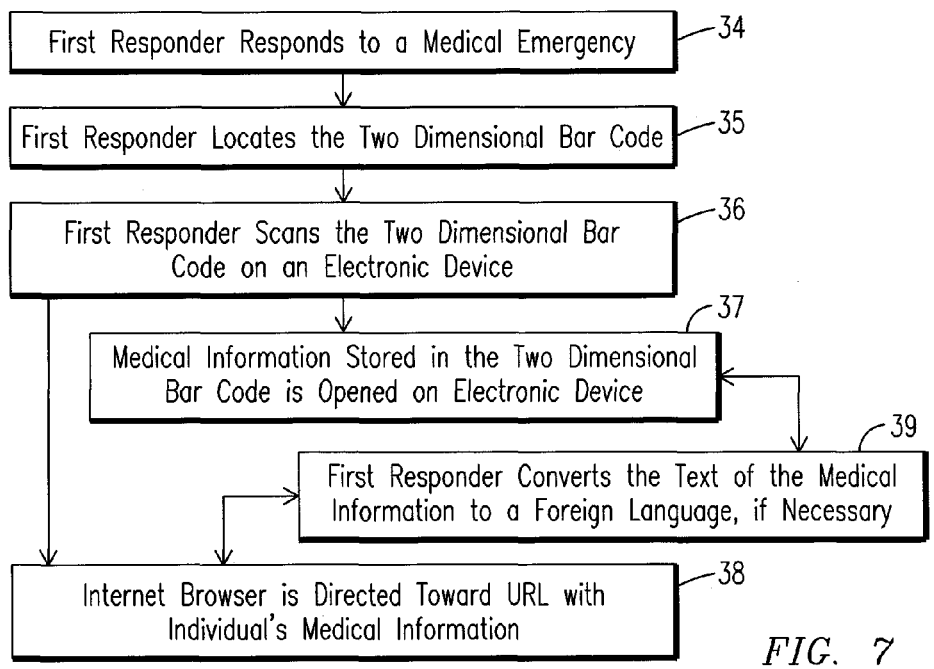
FIG. 7 is a flowchart showing the system and method of the present invention in which a first responder retrieves medical information from a patient's medical information device.

With reference to FIG. 7, a flowchart showing the system and method of the present invention in which a first responder retrieves medical information from a patient's medical information device is illustrated. First, a first responder responds to a medical emergency 34. Then, the first responder locates the two dimensional bar code 35. Next, the first responder scans the two dimensional bar code using an electronic device 36. Then, the medical information stored in the two dimensional bar code as text is opened on the electronic device 37 and/or an Internet browser on the electronic device is directed to a URL where the individual's medical information stored in the central database is accessible 38. The first responder may also convert the medical information to a foreign language if the patient has been injured or is receiving medical care in a foreign country 39.

It is to be understood that while a preferred embodiment of the invention is illustrated, it is not to be limited to the specific form or arrangement of parts herein described and shown. It will be apparent to those skilled in the art that various changes may be made without departing from the scope of the inven-

Having thus described my invention, I claim:

1. A method for using a medical information device for storing medical information and providing medical information to first responders and medical personnel comprising the steps of:
   a. an individual providing the service provider with his or her contact information;
   a. the service provider reviewing the contact information and rendering a decision on whether to allow the individual to have an account;
   b. an individual creating an account with a service provider over the interne;
   c. the individual's medical information being provided to the service provider to be saved in a central database; the individual obtaining a two dimensional bar code;
   d. the individual obtaining an electronic storage means that is personalized to the individual's account; and
   e. a first responder obtaining an account with the service provider to allow the first responder to access the medical information provided to the service provider by the individual.

2. The method of claim 1 further comprising steps of:
   the service provider deciding to allow the individual to have an account; and
   the service provider creating an account and providing the individual with a username and password.

3. The method of claim 1 further comprising steps of:
   the first responder scanning the electronic storage means using an electronic device and obtaining the individual's medical information.

4. The method of claim 3 further comprising a step of:
   the first responder translating the medical information to a foreign language using the electronic device.

5. The method of claim 1 wherein:
   said electronic storage means is a two dimensional bar code.

6. A system for using a medical information device for storing medical information and providing medical information to first responders and medical personnel comprising:
   the individual providing the service provider with his or her contact information;
   the service provider reviewing the contact information and rendering a decision on whether to allow the individual to have an account;
   an individual creating an account with a service provider over the internet;
   the individual obtaining a medical information device;
   the individual's medical information being provided to the service provider to be saved in a central database; the individual obtaining a two dimensional bar code;
   the individual obtaining a sleeve having an electronic storage means located thereon that to the individual's account the individual obtaining an electronic storage means that is personalized to the individual's account; and
   a first responder obtaining an account with the service provider to allow the first responder to access the medical information provided to the service provider by the individual.

7. The system of claim 6 further comprising:
   the service provider deciding to allow the individual to have an account; and
   the service provider creating an account and providing the individual with a username and password.

8. The system of claim 6 further comprising:
   the first responder scanning the electronic storage means using an electronic device and obtaining the individual's medical information.

9. The system of claim 8 further comprising:
   the first responder translating the medical information to a foreign language using the electronic device.

10. The system of claim 6 wherein:
    said electronic storage means is a two dimensional bar code.

* * * * *